United States Patent
Ishiyama

(10) Patent No.: US 7,695,833 B2
(45) Date of Patent: Apr. 13, 2010

(54) SOLID BODY SURFACE EVALUATION METHOD, MAGNETIC DISK EVALUATION METHOD, MAGNETIC DISK, AND MANUFACTURING METHOD THEREOF

(75) Inventor: Masafumi Ishiyama, Singapore (SG)

(73) Assignees: Hoya Corporation, Tokyo (JP); Hoya Magnetics Singapore Pte. Ltd., Singapore (SG)

( * ) Notice: Subject to any disclaimer, the term of this patent is extended or adjusted under 35 U.S.C. 154(b) by 68 days.

(21) Appl. No.: 11/623,488

(22) Filed: Jan. 16, 2007

(65) Prior Publication Data

US 2007/0196698 A1    Aug. 23, 2007

Related U.S. Application Data

(62) Division of application No. 11/050,764, filed on Feb. 7, 2005, now Pat. No. 7,174,775.

(30) Foreign Application Priority Data

Feb. 6, 2004   (JP)   ................. 2004-30278

(51) Int. Cl.
*G11B 5/66* (2006.01)
(52) U.S. Cl. ..................................... 428/833.6
(58) Field of Classification Search ................. None
See application file for complete search history.

(56) References Cited

U.S. PATENT DOCUMENTS

| 3,618,374 | A |   | 11/1971 | Miller |
| 3,862,491 | A |   | 1/1975 | Richardson |
| 5,837,357 | A | * | 11/1998 | Matsuo et al. ............... 428/212 |
| 6,346,309 | B1 | * | 2/2002 | Daimon ..................... 428/64.1 |
| 6,589,641 | B1 | * | 7/2003 | Stirniman et al. ........... 428/216 |
| 2004/0185262 | A1 | * | 9/2004 | Shimokawa ................ 428/421 |
| 2004/0187565 | A1 |   | 9/2004 | Sutton |

FOREIGN PATENT DOCUMENTS

| DE | 3825416 A1 | 2/1990 |
| JP | 61-59241 A | 3/1986 |
| JP | 3-100916 A | 4/1991 |

(Continued)

OTHER PUBLICATIONS

Hare, E. F. et al. Properties of Films of Adsorbed Fluorinated Acids, vol. 58; received Sep. 4, 1953; pp. 236-239, Naval Research Laboratory, Washington 25, DC.

*Primary Examiner*—Holly Rickman
(74) *Attorney, Agent, or Firm*—Sughrue Mion, PLLC

(57) ABSTRACT

In a method of evaluating surface tension of a solid body surface, selection is made of at least three liquid samples having different surface tensions, and contact angles between the respective liquid samples and the solid body surface are measured. Thereby, a correlation between cosines (Y) of the contact angles and surface tensions (X) of the liquid samples is derived as a logarithmic function. Surface tension of the solid body surface is evaluated by the use of a value of X that is calculated by substituting 1 for Y in the correlation. When evaluated by the foregoing evaluation method, a magnetic disk has a surface where the value of X, when 1 is substituted for Y, is greater than 0 and no greater than 17 mN/m.

5 Claims, 8 Drawing Sheets

FOREIGN PATENT DOCUMENTS

| | | |
|---|---|---|
| JP | 5-40930 A | 2/1993 |
| JP | 5-266465 A | 10/1993 |
| JP | 11-283245 A | 10/1999 |
| JP | 2001-330574 A | 11/2001 |
| JP | 2002-190136 A | 7/2002 |
| JP | 2003-151233 A | 5/2003 |
| JP | 2004-37430 A | 2/2004 |
| SU | 1086141 A | 4/1984 |

* cited by examiner

SOLID BODY SURFACE EVALUATION METHOD, MAGNETIC DISK EVALUATION METHOD, MAGNETIC DISK, AND MANUFACTURING METHOD THEREOF

This is a divisional of application Ser. No. 11/050,764 filed Feb. 7, 2005 now U.S. Pat. No. 7,174,775. The entire disclosure(s) of the prior application(s), application number(s) Ser. No. 11/050,764 is hereby incorporated by reference.

This application claims priority to prior Japanese Patent Application No. 2004-30278, the disclosure of which is incorporated herein by reference.

BACKGROUND OF THE INVENTION

This invention relates to a method of evaluating the surface of a solid body, a method of evaluating a magnetic disk, a magnetic disk, and a manufacturing method thereof. More specifically, this invention relates to a magnetic disk that is reduced in surface energy to enable prevention of fly stiction in a flying height of a magnetic recording head being 10 nm or less, and a manufacturing method of the magnetic disk.

In various industrial fields, "wettability" of solid body surfaces is cited as an important concept.

Particularly, the property of repelling "water", i.e. "water repellency", is utilized in design and manufacture of all industrial products such as design of high molecular materials, surface treatment to paper and fiber surfaces, water repellent finish of glass surfaces, printing, and lubricant design for hard disk surfaces.

When a liquid contacts the surface of a solid body so as to be hemispheric and forms a contact angle, this contact angle is determined by equilibrium among surface tension of the liquid, surface energy of the solid body, and solid-liquid interfacial energy. Use is often made of a method that utilizes this principle and calculates a surface energy of a solid body surface from a contact angle of a liquid whose surface tension is known.

In general, as a standard of surface free energy of a solid body surface, use is made of a critical surface tension ($\gamma c$) of Zisman (e.g. see Document 1 "J. Phys. Chem.", vol. 58, pp. 236 (1954)). According to Zisman et al., the critical surface tension ($\gamma c$) is defined as follows. When contact angles of a solid body surface are measured with respect to a series of saturated hydrocarbon liquids having different surface tensions and cosines ($\cos \theta$) of the contact angles are plotted for the surface tensions, a straight line is formed. In this straight line, a value of surface tension at a point extrapolated to a point where the cosine ($\cos \theta$) of the contact angle becomes 1 (i.e. a point that is completely wet) is the critical surface tension ($\gamma c$).

As values of $\gamma c$ in documents, those about fluorine compounds are low. Among them, a perfluorolauric acid monomolecular film having —$CF_3$ oriented on its surface, which is described in the foregoing Document 1 published in 1954 by Zisman et al., is often cited even now as the one having the lowest value (6 mN/m). It is noted here that mN/m represents milli Newton/meter.

The foregoing critical surface tension ($\gamma c$) defined by Zisman et al. has a certain effectiveness even at present, but there are problems shown below.

(1) A relationship between surface tensions of liquids and $\cos \theta$ does not become a linear relationship particularly when the surface tensions of the liquids become large.

(2) Depending on the presence of a hydrogen bonding property, polarity, and nonpolarity possessed by liquids, plotted points are divided into groups and do not form one straight line.

In case where surface energy of a solid body surface is evaluated, it cannot be said that a method of deriving a critical surface tension only by nonpolar saturated hydrocarbon liquids defined by Zisman et al. shows the true surface energy because the influence of other polarity components and hydrogen bond components is ignored.

Further, when a contact angle of water is inversely calculated by the use of an approximate expression of linear extrapolation that derives a critical surface tension of a perfluorolauric acid monomolecular film using a series of saturated hydrocarbon liquids, $\cos \theta = -1.47$ is obtained, which obviously deviates from the natural laws.

On the other hand, at present, drastic technological innovation is required in information recording technique, particularly in magnetic recording technique following the development of the IT industry. In a magnetic disk installed in a magnetic disk device such as an HDD (hard disk drive), a technique that can achieve an information recording density of 100 Gbit/inch$^2$ or more is required. In this magnetic disk, conventionally, a magnetic layer serving for information recording is provided on a substrate and, on the magnetic layer, a protection layer for protecting the magnetic layer and a lubrication layer that relaxes interference from a flying magnetic head are provided.

In the demand for higher recording densities in recent years, various approaches have been attempted in order to achieve the information recording density of 100 Gbit/inch$^2$ or more. As one of them, in order to improve spacing loss to thereby increase the S/N ratio, it is required to narrow a gap (magnetic spacing) between a magnetic layer of a magnetic disk and a recording/reproducing element of a magnetic head to 20 nm or less. From the viewpoint of achieving this magnetic spacing, it is required that the thickness of a protection layer of the magnetic disk be reduced to 5 nm or less. It is further required that the flying height of the magnetic head is reduced to 10 nm or less. Moreover, it is required that an LUL system (load/unload system) capable of higher capacity is used as a start/stop mechanism of an HDD instead of the conventional CSS system.

Here, in the LUL system, upon stopping, a magnetic recording head is retreated to a slope bed called a ramp located outside a magnetic disk while, upon starting, the magnetic recording head is, after the magnetic disk starts rotation, slided from the ramp over the surface of the magnetic disk, and then recording/reproduction is carried out. Accordingly, the magnetic recording head does not contact and slide on the magnetic disk.

In this LUL system, it is not necessary to provide a contact/slide region (CSS zone) for the magnetic recording head on the surface of the magnetic disk, which is required in the CSS system conventionally used. Therefore, it is possible to ensure a wider area of a recording/reproduction region as compared with the CSS system and thus increase the recording capacity of the magnetic recording medium. Further, in the LUL system, since the magnetic disk and the magnetic recording head do not contact each other, it is not necessary provide texture for preventing contact adsorption, which is required in the CSS system, so that the surface of the magnetic disk can be made even smoother. Therefore, the recording density of the magnetic disk can be increased by reducing the flying height of the magnetic recording head as compared with the CSS system.

In particular, recently, a magnetic disk apparatuses such as HDDs (hard disk drives) are often used in environments of low atmospheric pressures such as in an airplane. Following this, there has been arising a problem about flying stability of magnetic heads. Specifically, the flying height of the magnetic head further decreases from 10 nm due to a change in atmospheric pressure and, further, there is variation in flying height due to processing accuracy of air bearing sliders of the magnetic heads. As a result, a problem of fly stiction has occurred frequently. The fly stiction is a trouble where the flying posture and height of the magnetic recording head go out of order during its flying operation and irregular changes in reproduction output occur frequently. According to circumstances, the magnetic recording head is brought into contact with the magnetic disk so as to crash during the flying operation, thereby destroying the magnetic disk. This fly stiction often occurs without a premonitory sign and is one of troubles that are difficult to control. As a cause for occurrence of the fly stiction, there can be considered the influence of roughness of the surface of the magnetic disk, interaction (meniscus force) between a lubrication layer and the head, or contamination due to outgas from the magnetic disk device.

According to the study by the present inventors, it has been found that the foregoing fly stiction phenomenon has a close relationship with surface energy of the magnetic disk surface. Specifically, the mechanism for preventing the fly stiction phenomenon is as follows. By reducing the surface energy of the magnetic disk surface, the magnetic disk surface changes to a more inactive state. Because of the inactive surface, the interaction with the magnetic recording head becomes small and further the outgas from the magnetic disk apparatus cannot easily adhere to the magnetic disk surface so that the flying stability of the magnetic recording head increases.

SUMMARY OF THE INVENTION

Under such circumstances, it is an object of this invention to provide a solid body surface evaluation method that solves the problem inherent to the critical surface tension ($\gamma c$) proposed by Zisman et al. as a standard of surface free energy of a solid body surface and effectively evaluates surface tension of a solid body surface, and a magnetic disk evaluation method that evaluates surface tension of a magnetic disk surface by the use of the solid body surface evaluation method.

It is another object of this invention to provide a magnetic disk that is reduced in surface energy to enable prevention of fly stiction in a flying height of a magnetic recording head being 10 nm or less, and a manufacturing method of the magnetic disk.

As a result of assiduously repeating studies in order to achieve the foregoing objects, the present inventors have measured contact angles of a solid body surface by the use of at least three liquids having different surface tensions and derived a correlation between cosines of the contact angles and surface tensions of the liquids as a logarithmic function. As a result, they have found that there can be obtained an approximate expression having a correlation coefficient higher than that of the conventional linear approximation proposed by Zisman et al. and the surface tension of the solid body surface can be univocally defined by the use of the liquids having different components.

They have selected a nonpolar substance, a polar substance, and a hydrogen bonding substance as the foregoing at least three liquids having the different surface tensions and, using these liquids, measured contact angles of the solid body surface and derived a correlation between cosines of the contact angles and surface tensions of the liquids. They have found that, by utilizing it, the surface tension of the solid body surface can be effectively evaluated.

Further, a lubrication layer is provided such that a value of the surface tension of the liquid, when the cosine of the contact angle ($\cos \theta$) becomes 1, becomes a predetermined value in the approximate expression obtained as described above. They have found that this makes it possible to obtain a magnetic disk with reduced surface energy and prevent fly stiction in a flying height of a magnetic recording head being 10 nm or less.

This invention has been completed on the basis of the foregoing knowledge.

Specifically, this invention has the following structures.

(Structure 1)

A solid body surface evaluation method for evaluating a solid body surface, comprising: selecting at least three liquid samples having different surface tensions, measuring contact angles between the respective liquid samples and the solid body surface to thereby derive a correlation between cosines (Y) of the contact angles and surface tensions (X) of the liquid samples as a logarithmic function, and evaluating surface tension of the solid body surface by the use of a value of X that is calculated by substituting 1 for Y in the correlation (hereinafter referred to as a solid body surface evaluation method I).

(Structure 2)

A solid body surface evaluation method of the foregoing structure 1, wherein: the at least three liquid samples having the different surface tensions include a liquid sample containing a nonpolar substance, a liquid sample containing a polar substance, and a liquid sample containing a hydrogen bonding substance.

(Structure 3)

A solid body surface evaluation method for evaluating a solid body surface, comprising: selecting at least three liquid samples including a liquid sample containing a nonpolar substance, a liquid sample containing a polar substance, and a liquid sample containing a hydrogen bonding substance, and having mutually different surface tensions, measuring contact angles between the respective liquid samples and the solid body surface to thereby derive a correlation between cosines (Y) of the contact angles and surface tensions (X) of the liquid samples, and evaluating surface tension of the solid body surface by the use of a value of X that is calculated by substituting 1 for Y in the correlation (hereinafter referred to as a solid body surface evaluation method II).

(Structure 4)

A magnetic disk evaluation method for evaluating a surface of a magnetic disk having at least a magnetic layer, a protection layer, and a lubrication layer formed on a substrate in this order, comprising: evaluating surface tension of the surface of the magnetic disk based on the solid body surface evaluation method of any of the foregoing structures 1 to 3.

(Structure 5)

A magnetic disk having at least a magnetic layer, a protection layer, and a lubrication layer formed on a substrate in this order, wherein: when selection is made of at least three liquid samples including a liquid sample containing a nonpolar substance, a liquid sample containing a polar substance, and a liquid sample containing a hydrogen bonding substance, and having mutually different surface tensions, contact angles between the respective liquid samples and a surface of the magnetic disk are measured to thereby derive a correlation between cosines (Y) of the contact angles and surface tensions (X) of the liquid samples as a natural logarithmic function by a method of least squares, and a value of X that is calculated by substituting 1 for Y in the correlation is given as a true critical surface tension of the magnetic disk, the true critical surface tension is greater than 0 and no greater than 17 mN/m.

(Structure 6)

A magnetic disk of the foregoing structure 5, wherein: a surface tension of a lubricant forming the lubrication layer is 20 mN/m or less.

(Structure 7)

A magnetic disk of the foregoing structure 5 or 6, wherein: the lubrication layer contains a perfluoropolyether compound having hydroxyl groups as terminal functional groups.

(Structure 8)

A magnetic disk of the foregoing structure 5 or 6, wherein: the protection layer is a carbon-based protection layer containing hydrogen atoms and/or nitrogen atoms.

(Structure 9)

A magnetic disk of the foregoing structure 5 or 6, wherein: the magnetic disk is for installation in a hard disk drive of a load/unload system.

(Structure 10)

A manufacturing method of a magnetic disk for forming at least a magnetic layer, a protection layer, and a lubrication layer on a substrate in this order, comprising: selecting at least three liquid samples including a liquid sample containing a nonpolar substance, a liquid sample containing a polar substance, and a liquid sample containing a hydrogen bonding substance, and having mutually different surface tensions, measuring contact angles between the respective liquid samples and a surface of the magnetic disk to thereby derive a correlation between cosines (Y) of the contact angles and surface tensions (X) of the liquid samples as a natural logarithmic function by a method of least squares and, when a value of X calculated by substituting 1 for Y in the correlation is a true critical surface tension of the magnetic disk, providing the lubrication layer by forming a film of a lubricant containing a perfluoropolyether compound refined to a predetermined molecular weight such that the true critical surface tension becomes greater than 0 and no greater than 17 mN/m.

(Structure 11)

A manufacturing method of a magnetic disk of the foregoing structure 10, wherein: the protection layer is deposited by a plasma CVD method using a hydrocarbon gas as a material gas.

According to this invention, it is possible to provide a solid body surface evaluation method that measures contact angles of a solid body surface by the use of at least three liquids having different surface tensions, derives a correlation between cosines of the contact angles and surface tensions of the liquids and, by utilizing it, evaluates the surface tension of the solid body surface.

Further, according to this invention, it is possible to provide a magnetic disk evaluation method for evaluating surface tension of the surface of a magnetic disk by the use of the foregoing solid body surface evaluation method, a magnetic disk that is formed with a lubrication layer by applying the foregoing solid body surface evaluation method so as to be reduced in surface energy to thereby enable prevention of fly stiction in a flying height of a magnetic recording head being 10 nm or less, and a manufacturing method of the magnetic disk.

DETAILED DESCRIPTION OF THE PREFERRED EMBODIMENT

Figure 1:
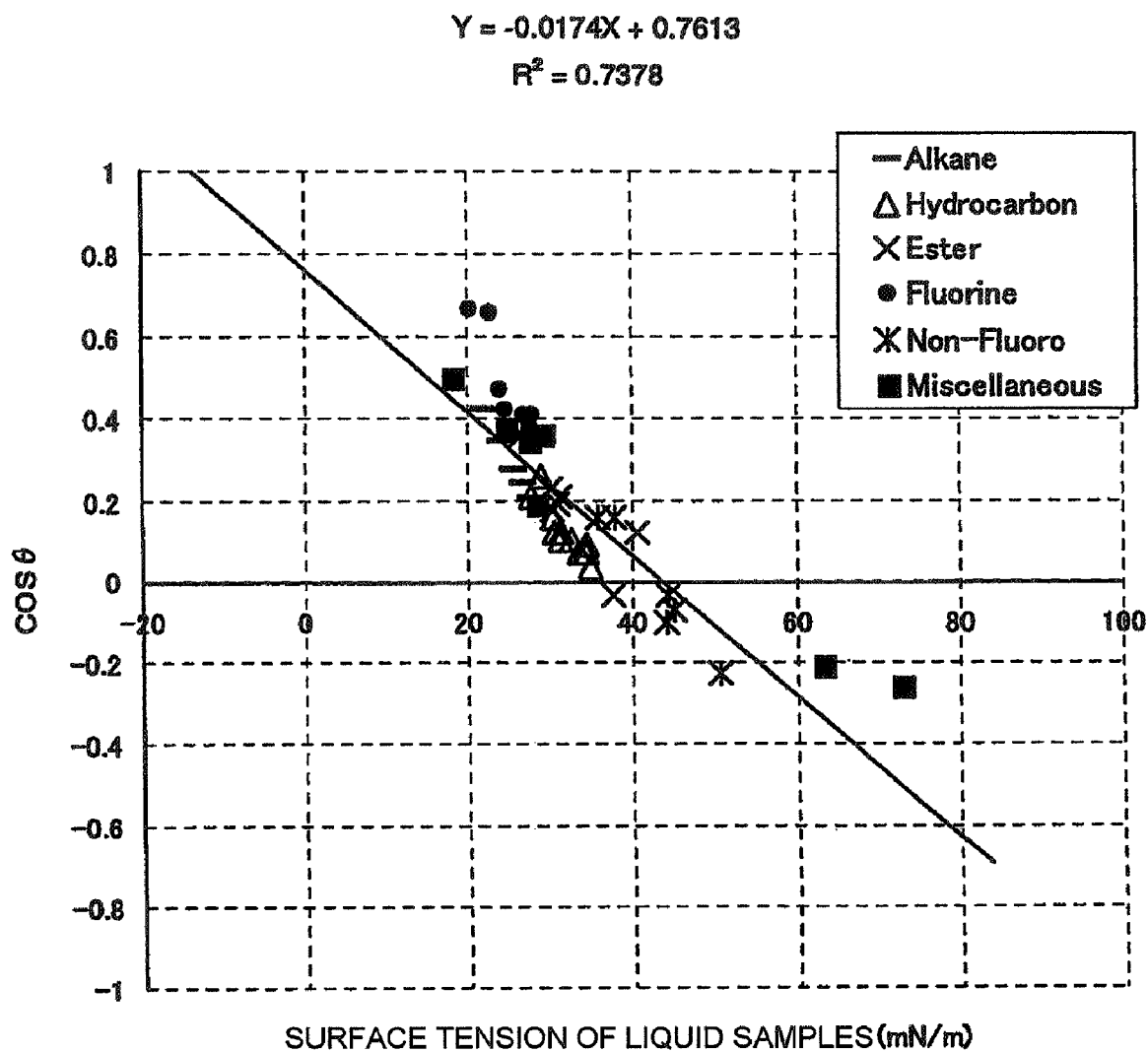
FIG. 1 is a graph showing an example of the Zisman method when data given in the foregoing Document 1 are all plotted and a relationship between surface tensions of liquids and cosines of contact angles is linearly approximated.

First, description will be given of a solid body surface evaluation method of this invention.

The solid body surface evaluation method of this invention includes two modes, i.e. a solid body surface evaluation method I and a solid body surface evaluation method II.

The solid body surface evaluation method I is a method that selects at least three liquid samples having different surface tensions, measures contact angles between the respective liquid samples and a solid body surface to thereby derive a correlation between cosines (Y) of the contact angles and surface tensions (X) of the liquid samples as a logarithmic function, and evaluates surface tension of the solid body surface by the use of a value of X that is calculated by substituting 1 for Y in the foregoing correlation.

In the solid body surface evaluation method I, as the three liquid samples having the different surface tensions, use is preferably made of those samples each containing a nonpolar substance, a polar substance, and a hydrogen bonding substance. Then, it is advantageous to derive the correlation between the cosines (Y) of the contact angles and the surface tensions (X) of the liquid samples as a natural logarithmic function by the method of least squares, i.e. to derive an approximate expression given by $$Y = a + \ln(X) + b \tag{1}$$

[X is a surface tension (mN/m) of the liquid sample, Y is a cosine ($\cos \theta$) of the contact angle, and a and b are constants.].

In this invention, a value of X (surface tension of liquid sample) when Y ($\cos \theta$) becomes 1 (i.e. a point that is completely wet) in the foregoing approximate expression (1) is defined as "a true critical surface tension".

In the case of Zisman-plot (linear approximation), the critical surface tension changes depending on a liquid that is used, and may exhibit a minus once in a while. The surface tension exhibiting a minus is physically not possible and therefore, clearly, it cannot be said that this Zisman-plot shows the true surface state. However, in the case of using the logarithmic approximation as in this invention, the surface tension never shows a minus. Further, it has been found that when correlation coefficients $R^2$ are compared between the linear approximation and the logarithmic approximation, the correlation coefficient $R^2$ is higher in the case of the logarithmic approximation and, therefore, accuracy of the approximate expression is higher than that of the linear approximation.

Further, in Zisman-plot, it is necessary to select liquids used in contact angle measurement so that the critical surface tension becomes maximum. However, in the system of this invention, there is an advantage in that selection of liquids is not necessary and, by using three kinds of hydrogen bonding, polar, and nonpolar liquid samples, the surface tension of the solid body surface can be determined univocally.

In a method of measuring the surface in terms of properties only by the van der Waals force, when a surface energy of the solid body surface is determined, it is possible to judge a critical point with respect to the van der Waals force, but all surface energies do not necessarily represent that critical point. Therefore, in the conventional Zisman method using various liquids to select those liquids that give the maximum critical surface tension through trial and error, loss in time and cost is quite large and, further, the obtained results cannot always explain all the surface energies. Moreover, according to circumstances, the critical surface tension may be excessively evaluated, thus causing a practical problem.

In contrast, according to the method of this invention, not only the true critical surface tension can be derived by extrapolation of the logarithmic approximate expression, but also a value of a contact angle, when a liquid sample providing a certain surface tension is used, can be estimated from the approximate expression, thus being quite beneficial.

Figure 2:
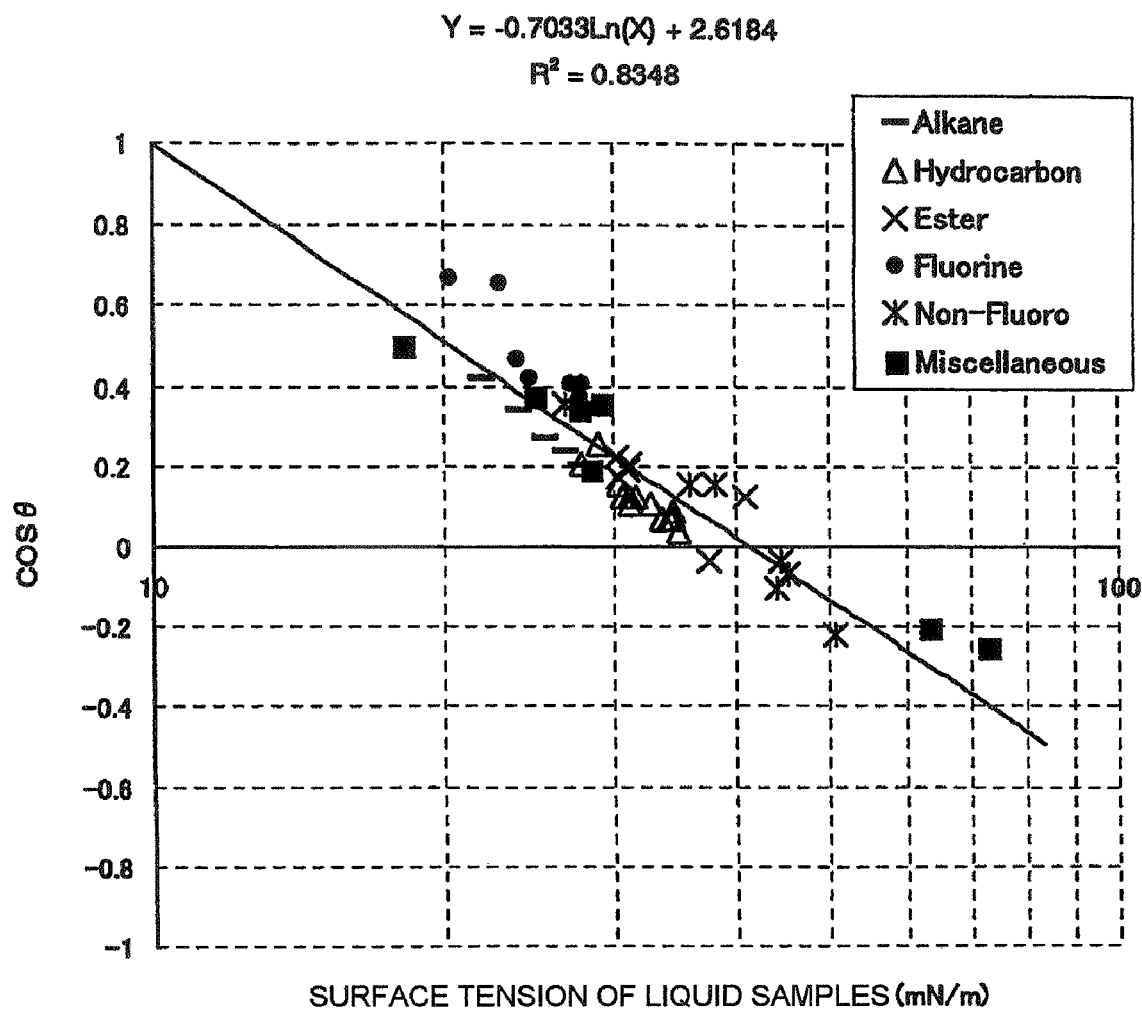
FIG. 2 is a graph showing an example of a method of this invention when data given in the foregoing Document 1 are all plotted and a relationship between surface tensions of liquids and cosines of contact angles is logarithmically approximated.

FIG. 1 shows an example of the Zisman method when data given in the foregoing Document 1 are all plotted and a relationship between surface tensions of liquids and cosines of contact angles is linearly approximated. FIG. 2 shows an example of the method of this invention when data given in Document 1 are all plotted and a relationship between surface tensions of liquids and cosines of contact angles is logarithmically approximated.

As seen from FIG. 1, in case where the linear approximation is performed using all kinds of liquids according to the Zisman method, the critical surface tension extrapolated to a point where a cosine becomes 1 (i.e. a point that is completely wet) becomes minus. Further, it is clear that large deviation from the linear approximation occurs in a region of high surface tension.

On the other hand, as seen from FIG. 2, in case where the logarithmic approximation is performed according to the method of this invention, distribution follows relatively along the logarithmic approximation curve from low to high surface tension regions and a correlation coefficient thereof is higher as compared with that of the linear approximation in the Zisman method. That is, it can be said that approximation accuracy is higher in the logarithmic approximation.

On the other hand, the solid body surface evaluation method II is a method that selects at least three liquid samples including a liquid sample containing a nonpolar substance, a liquid sample containing a polar substance, and a liquid sample containing a hydrogen bonding substance, and having mutually different surface tensions, measures contact angles between the respective liquid samples and a solid body surface to thereby derive a correlation between cosines (Y) of the contact angles and surface tensions (X) of the liquid samples, and evaluates surface tension of the solid body surface by the use of a value of X that is calculated by substituting 1 for Y in the foregoing correlation.

In the solid body surface evaluation method II, at least three liquid samples including the liquid sample containing the nonpolar substance, the liquid sample containing the polar substance, and the liquid sample containing the hydrogen bonding substance, and having mutually different surface tensions are selected as the liquid samples and used. Then, like in the foregoing solid body surface evaluation method I, the correlation between the cosines (Y) of the contact angles and the surface tensions (X) of the liquid samples is derived.

In this case, the correlation may be derived by a function other than a logarithmic function. It is important to derive a function that makes a correlation coefficient $R^2$ as high as possible. Then, in this function, the surface tension of the solid body surface is evaluated by the use of a value of X that is calculated by substituting 1 for Y.

This invention also provides a magnetic disk evaluation method that evaluates surface tension of the surface of a magnetic disk having at least a magnetic layer, a protection layer, and a lubrication layer formed on a substrate in this order, by the use of the foregoing solid body surface evaluation method I or II.

Now, a magnetic disk of this invention will be described.

In a magnetic disk apparatus, various plastic materials, adhesives, and metal processed materials are used as internal apparatus materials. In this case, outgases from those materials may be expected to contaminate the surface of the magnetic disk. In particular, in an environment of high temperature and high humidity, emission of the outgases is accelerated to cause contamination of the magnetic disk surface. It is considered that the outgases emitted are organic matter contamination (silicone, DOP, DBP, etc.), inorganic matter contamination (amine, phosphoric acid, etc.), and water vapor. Under such circumstances, design should be carried out so that adhesion to the magnetic disk surface is difficult for the contamination in any energy states.

The magnetic disk of this invention is a magnetic disk having at least a magnetic layer, a protection layer, and a lubrication layer formed on a substrate in this order and has the following features. Selection is made of at least three liquid samples including a liquid sample containing a nonpolar substance, a liquid sample containing a polar substance, and a liquid sample containing a hydrogen bonding substance, and having mutually different surface tensions, and contact angles between the respective liquid samples and the surface of the magnetic disk are measured. Thereby, a correlation between cosines (Y) of the contact angles and surface tensions (X) of the liquid samples is derived as a natural logarithmic function given as the foregoing approximate expression (1) by the use of the method of least squares. In this approximate expression (1), a value of X (true critical surface tension of the magnetic disk) calculated by substituting 1 for Y is greater than 0 and no greater than 17 mN/m. When this true critical surface tension exceeds 17 mN/m, the fly stiction cannot be sufficiently prevented in a flying height of a magnetic recording head being 10 nm or less. The true critical surface tension is preferably 10 to 16 mN/m.

In the magnetic disk of this invention, in order to achieve the true critical surface tension of 17 mN/m or less, it is important that the surface tension of a lubricant forming the lubrication layer is set to 20 mN/m or less, preferably 19.5 mN/m or less. By reducing the surface tension of the lubricant itself, low surface tension is exhibited even after applied to the magnetic disk.

The protection layer in the magnetic disk of this invention is not particularly limited but, preferably, it is a protection layer made of amorphous carbon and has the following structure. It is preferable that at least a carbon-based protection layer formed on the side of the magnetic layer is an amorphous diamond-like carbon protection layer formed by CVD. By the use of the diamond-like carbon protection layer, suitable hardness and durability can be obtained.

In this invention, there is no particular limitation to CVD (Chemical Vapor Deposition) but it is preferable that the carbon-based protection layer is formed by plasma CVD (P-CVD) that uses plasma to excite atoms. The carbon-based protection layer formed by P-CVD is high in fineness and hardness and can suitably prevent metal ions of the magnetic layer from migrating to the magnetic disk surface and, therefore, it is particularly preferable as a thin-film protection layer. In case where the carbon-based protection layer is formed by P-CVD, it is preferable that diamond-like carbon is formed using a hydrocarbon gas as a reactive gas.

As the reactive gas, it is preferable to use low-grade hydrocarbon. Particularly, use is preferably made of any of low-grade saturated hydrocarbon, low-grade unsaturated hydrocarbon, and low-grade ring hydrocarbon. As the low-grade saturated hydrocarbon, use can be made of methane, ethane, propane, butane, octane, or the like. As the low-grade unsaturated hydrocarbon, use can be made of ethylene, propylene, butylene, acetylene, or the like. As the low-grade ring hydrocarbon, use can be made of benzene, toluene, xylene, styrene, naphthalene, cyclohexane, or the like. It is noted here that low-grade referred to herein represents hydrocarbon where the number of carbons per molecule is 1 to 10. The reason why use of the low-grade hydrocarbon is preferable is that as the number of carbons increases, it becomes difficult to vaporize it into gas and supply it to a film-forming apparatus and, in addition, it becomes difficult to decompose it during plasma discharge. Further, when the number of carbons increases, high-molecular hydrocarbon components tend to be largely contained in components of the formed protection layer to thereby reduce the fineness and hardness of the protection layer, which is thus not preferable. In view of this, it is preferable to use the low-grade hydrocarbon as hydrocarbon. It is particularly preferable to use the low-grade unsaturated hydrocarbon because a fine and high-hardness carbon-based protection layer can be formed. In view of this, acetylene is particularly preferable.

It is preferable that the carbon-based protection layer formed by CVD is a protection layer of hydrogenated diamond-like carbon. By the use of hydrogenated diamond-like carbon, the fineness of the protection layer can be further improved and the hardness thereof can also be improved, which is particularly preferable for this invention. In this case, it is preferable that the content of hydrogen is set to 3 atm % or more and less than 20 atm % relative to the total of the protection layer when measuring the carbon-based protection layer by HFS (Hydrogen Forward Scattering). When the content of hydrogen is less than 3 atm %, the fineness is often lowered and therefore the migration of metal ions cannot be prevented. Further, since the hardness is often lowered, the magnetic layer cannot be suitably protected from an impulsive force upon the start of LUL. On the other hand, when the content of hydrogen is 20 atm % or more, polymeric carbon components often increase so as to reduce adhesion performance of the protection layer with respect to the magnetic layer and therefore the protection layer is stripped off upon the start of LUL, which is thus not preferable.

It is further preferable to use a carbon nitride protection layer or a hydrogenated carbon nitride protection layer which is in the form of a carbon-based protection layer containing nitrogen. This is because, by the inclusion of nitrogen, it is possible to highly promote orientation of terminal polar groups of the lubricant toward the side of the protection layer. The content of nitrogen relative to carbon can be 4 to 12 atm % in case where measurement is carried out by XPS (X-ray Photoelectron Spectroscopy).

In this invention, the thickness of the carbon-based protection layer formed by CVD is preferably 1 to 5 nm. When less than 1 nm, it may not be sufficient to prevent the migration of metal ions of the magnetic layer, and therefore, there is a problem in abrasion resistance. Although it is not necessary to particularly provide an upper limit to the thickness of the carbon-based protection layer formed by CVD, it is preferably set to 5 nm or less on a practical basis so as not to impede the improvement in magnetic spacing.

In this invention, the lubrication layer is preferably made of molecular weight fractionated perfluoropolyether having hydroxyl groups as terminal groups. Perfluoropolyether has a straight chain structure to thereby exhibit proper lubrication performance for the magnetic disk and, because of including hydroxyl groups (OH) as terminal groups, it can demonstrate high adhesion performance with respect to the carbon-based protection layer. Particularly, in the case of containing nitrogen on the surface of the carbon-based protection layer, since ($N^+$) and ($OH^-$) exhibit high affinity, high adhesion rate of the lubrication layer can be achieved, which is thus preferable. Further, the molecular weight fractionation makes it possible to remove impurity components of various alcohol denatured perfluoropolyether compounds such as a monool compound, a diol compound, a triol compound, and a tetraol compound that are contained.

As the perfluoropolyether compound having hydroxyl groups as terminal groups, it is preferable that the number of hyroxyl groups per molecule is 2 to 4. When less than two, the adhesion rate of the lubrication layer is often lowered, and therefore, it is not preferable. When exceeding four, the lubrication performance is often reduced due to excessive improvement in adhesion rate. Although there is no particular limitation to molecular weight distribution of the perfluoropolyether compound, it may be 5000 or more, particularly 5800 or more at weight average molecular weight (Mw). The thickness of the lubrication layer may be properly adjusted within the range of 0.5 to 1.5 nm. When less than 0.5 nm, the lubrication performance is often reduced, while, when exceeding 1.5 nm, the adhesion rate of the lubrication layer is often lowered.

In this invention, it is preferable that, after depositing the lubrication layer, the surface of the lubrication layer, i.e. the surface of the magnetic disk, is treated with hydrofluoroether (HFE). Specifically, it is preferable to perform a treatment where HFE is brought into contact with the magnetic disk having been formed with the lubrication layer. For example, the treatment can be carried out by a vapor deposition method, an immersion method, or the like. Through the treatment in this manner, HFE is deposited on the surface of the lubrication layer of the magnetic disk.

The hydrofluoroether compound used in the HFE treatment is preferably a compound having a molecular weight of about 150 to 400. Particularly, it is preferable to select a compound having a molecular weight of 350 or less. Specifically, use can be preferably made of $C_4F_9$—O—$CH_3$ and/or $C_4F_9$—O—$C_2H_5$. Further, the surface tension of hydrofluoroether is preferably set greater than 0 and no greater than 14 mN/m.

In this invention, a glass substrate is preferably used as the substrate. Since the glass substrate can achieve smoothness and high rigidity, the magnetic spacing, particularly the flying height of the magnetic head, can be reduced more stably, which is thus particularly preferable in this invention. As a material of the glass substrate, aluminosilicate glass is particularly preferable. Aluminosilicate glass can achieve high rigidity and strength by chemical strengthening.

In this invention, the surface roughness of the magnetic disk surface is preferably 4 nm or less in Rmax and 0.4 nm or less in Ra. When Rmax exceeds 4 nm, the reduction in magnetic spacing is often impeded, which is thus not preferable. It is noted here that the surface roughness referred to herein is defined in Japanese Industrial Standard (JIS) B0601.

The magnetic disk of this invention can be suitably used for installation in an HDD of the LUL system.

Figure 3:
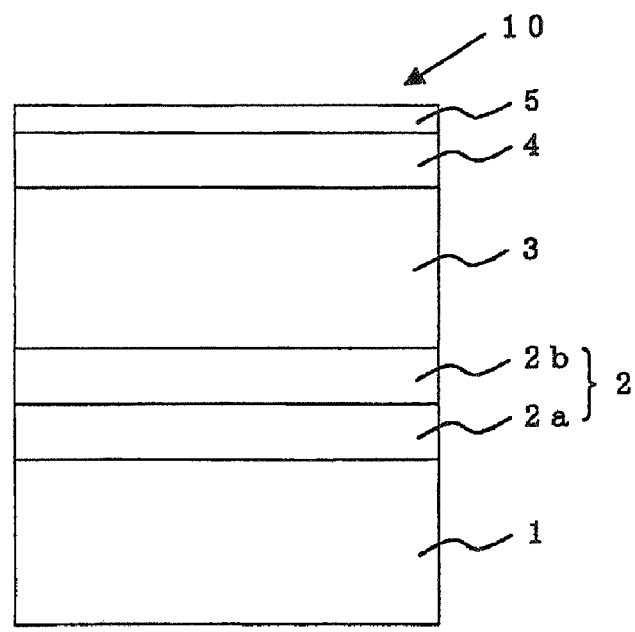
FIG. 3 is a sectional view exemplarily showing one example of a layer structure of a magnetic disk of this invention.

FIG. 3 is a sectional view exemplarily showing one example of a layer structure of a magnetic disk of this invention. This magnetic disk 10 comprises at least a substrate 1, a magnetic layer 3 formed on the substrate, a carbon-based protection layer 4 formed on the magnetic layer 3, and a lubrication layer 5 formed on the protection layer 4. In this embodiment, the magnetic layer 3 and the carbon-based protection layer 4 are formed so as to contact each other and the carbon-based protection layer 4 and the lubrication layer 5 are formed so as to contact each other. Between the substrate 1 and the magnetic layer 3, a nonmagnetic metal layer 2 composed of a seed layer 2a and an underlayer 2b is formed. In the magnetic disk 10, all except the magnetic layer 3 are nonmagnetic bodies.

Subsequently, a magnetic disk manufacturing method of this invention will be described.

In the magnetic disk manufacturing method of this invention, the magnetic disk 10 is manufactured by forming at least the magnetic layer 3, the protection layer 4, and the lubrication layer 5 on the substrate 1 in this order. In this event, selection is made of at least three liquid samples including a liquid sample containing a nonpolar substance, a liquid sample containing a polar substance, and a liquid sample containing a hydrogen bonding substance, and having mutually different surface tensions. Then, contact angles between the respective liquid samples and the surface of the magnetic disk are measured. Thereby, a correlation between cosines (Y) of the contact angles and surface tensions (X) of the liquid samples is derived as a natural logarithmic function given as the foregoing approximate expression (1) by the use of the method of least squares. A lubricant containing a perfluoropolyether compound refined to a predetermined molecular weight is deposited so that a value of X (true critical surface tension of the magnetic disk) calculated by substituting 1 for Y in the approximate expression (1) becomes greater than 0 and no greater than 17 mN/m, preferably 10 to 16 mN/m. In this manner, the lubrication layer 5 is formed.

Further, the protection layer 4 is preferably deposited by the plasma CVD method that uses a hydrocarbon gas as a material gas.

EXAMPLES

Now, this invention will be described in further detail by the use of examples, but this invention is not limited at all by those examples.

Example 1

53 kinds of magnetic disks having different kinds of lubricants, different thicknesses, and different kinds of carbon-based protection films were prepared. Each of these magnetic disks is a magnetic disk that is incorporated into a hard disc drive and has an outermost surface where perfluoropolyether is applied to a thickness of 1.0 to 1.5 nm.

Lubricants of magnetic disks used in recent magnetic recording devices are used in environments of high rotational speeds, high temperatures and high humidities and are thus required to maintain inactive surface states. The surface tension of the surface of each of these magnetic disks was measured according to the following method.

As liquids that were used, selection was made of the following five kinds whose surface tensions were known.

hydrogen bonding liquid $H_2O$ (water): 72.8 mN/m
polar liquid $CH_2I_2$ (methylene iodide): 50.8 mN/m,
$C_2H_6O_2$ (ethylene glycol): 48.0 mN/m
nonpolar liquid $C_{14}H_{30}$ (tetradecane): 26.7 mN/m,
$C_6H_{14}$ (hexane): 20.4 mN/m Note that hydrogen bonding, polar, and nonpolar liquids are not limited to the foregoing.

First, 1 µL of the foregoing liquid was dropped onto the surface of the magnetic disk and a contact angle was measured after 10 seconds from dropping. The liquid amount was set to 1 µL because each liquid exhibited a substantially constant contact angle at 1 µL or more regardless of the sample. Duplicate measurement was carried out twice per liquid and the mean value thereof was derived as a contact angle. For the contact angle measurement, use was made of a contact angle measuring system "VCA Video Contact Angle System" of Analytical Technology Incorporated. After the measurement, cosines (cos θ) of the obtained contact angles were derived and plotted against values of the surface tensions of the respective liquids.

A natural logarithm given as Y=a×ln (X)+b was used as an approximate expression with respect to the respective plots and coefficients a and b were determined by the use of the method of least squares where the sum of squares of errors becomes minimum, thereby approximating the plots. Then, the logarithmically approximated curve was extrapolated to derive a value of surface tension at a point extrapolated to a point where the cosine (cos θ) becomes 1 (i.e. a point that is completely wet) and this value was given as a true critical surface tension of the magnetic disk surface.

Figure 4:
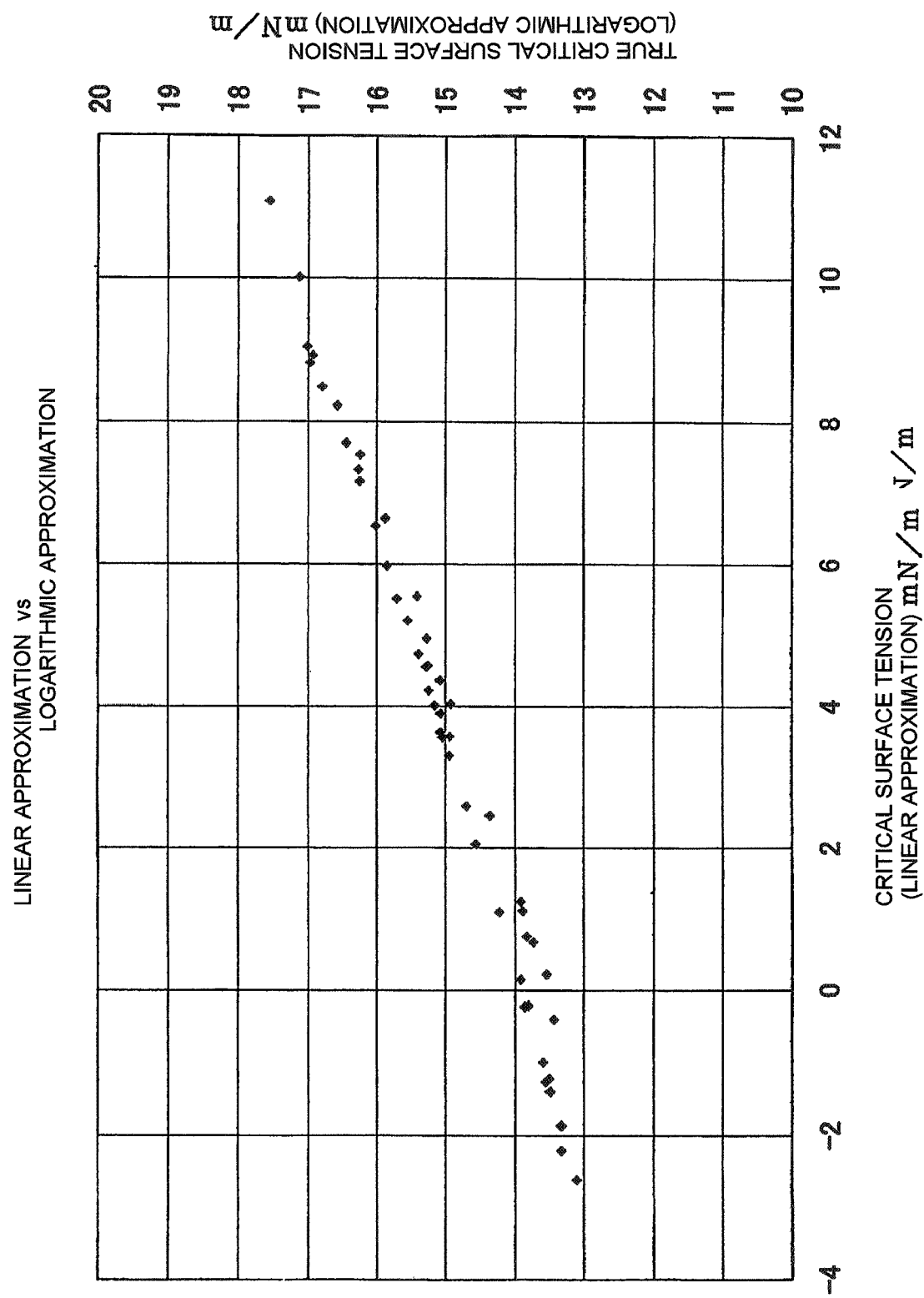
FIG. 4 is a plot diagram showing a relationship between critical surface tensions by linear approximation and true critical surface tensions by logarithmic approximation with respect to respective magnetic disks in Example 1.

FIG. 4 shows a relationship between critical surface tensions by linear approximation and true critical surface tensions by logarithmic approximation with respect to the 53 kinds of magnetic disks.

The relationship between the critical surface tensions by linear approximation and the true critical surface tensions by logarithmic approximation becomes a substantially linear relationship in a region where the critical surface tensions are large while the straight line becomes dull in a low region. This is because the true critical surface tensions are based on logarithmic approximation. However, it is understood that, with respect to the critical surface tensions and the true critical surface tensions, order of magnitudes thereof, i.e. a magnitude relationship thereof, is unchanged and maintained. The critical surface tensions often take minus values and, also in terms of it, it may be gathered that the true critical surface tensions are effective.

Figure 5:
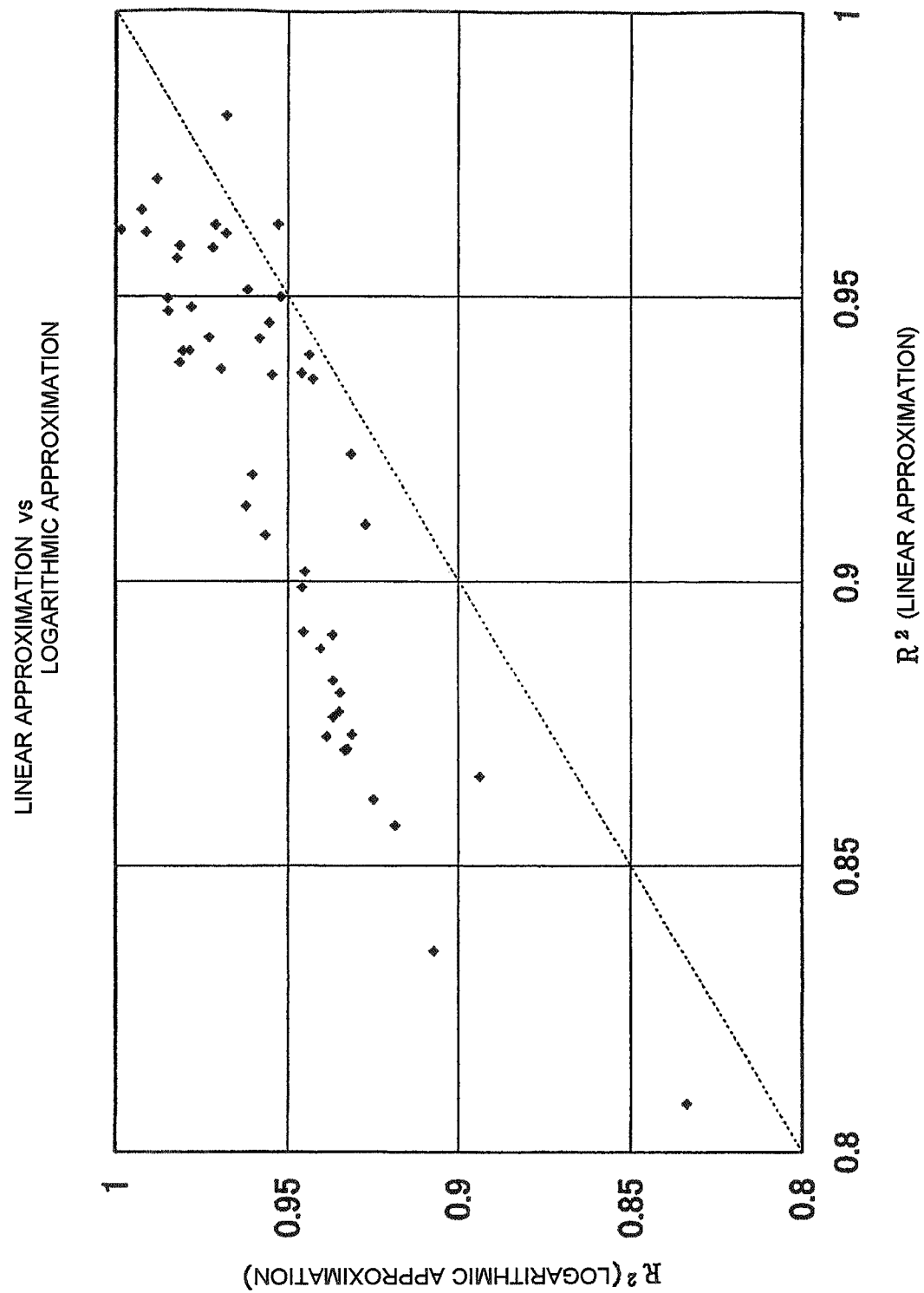
FIG. 5 is a plot diagram showing a relationship between correlation coefficients each obtained when a relationship between surface tensions of liquids and cosines of contact angles is approximated by linear approximation and correlation coefficients each obtained when approximated by logarithmic approximation in Example 1.

FIG. 5 shows a relationship between correlation coefficients when approximated by linear approximation and correlation coefficients when approximated by logarithmic approximation.

As clear from FIG. 5, it is understood that the correlation coefficients are higher in the case of logarithmic approximation as compared with linear approximation. Also in terms of this, it can be said that logarithmic approximation is excellent in univocally determining the surface tension of the solid body surface by the use of three kinds of different liquids.

Figure 6:
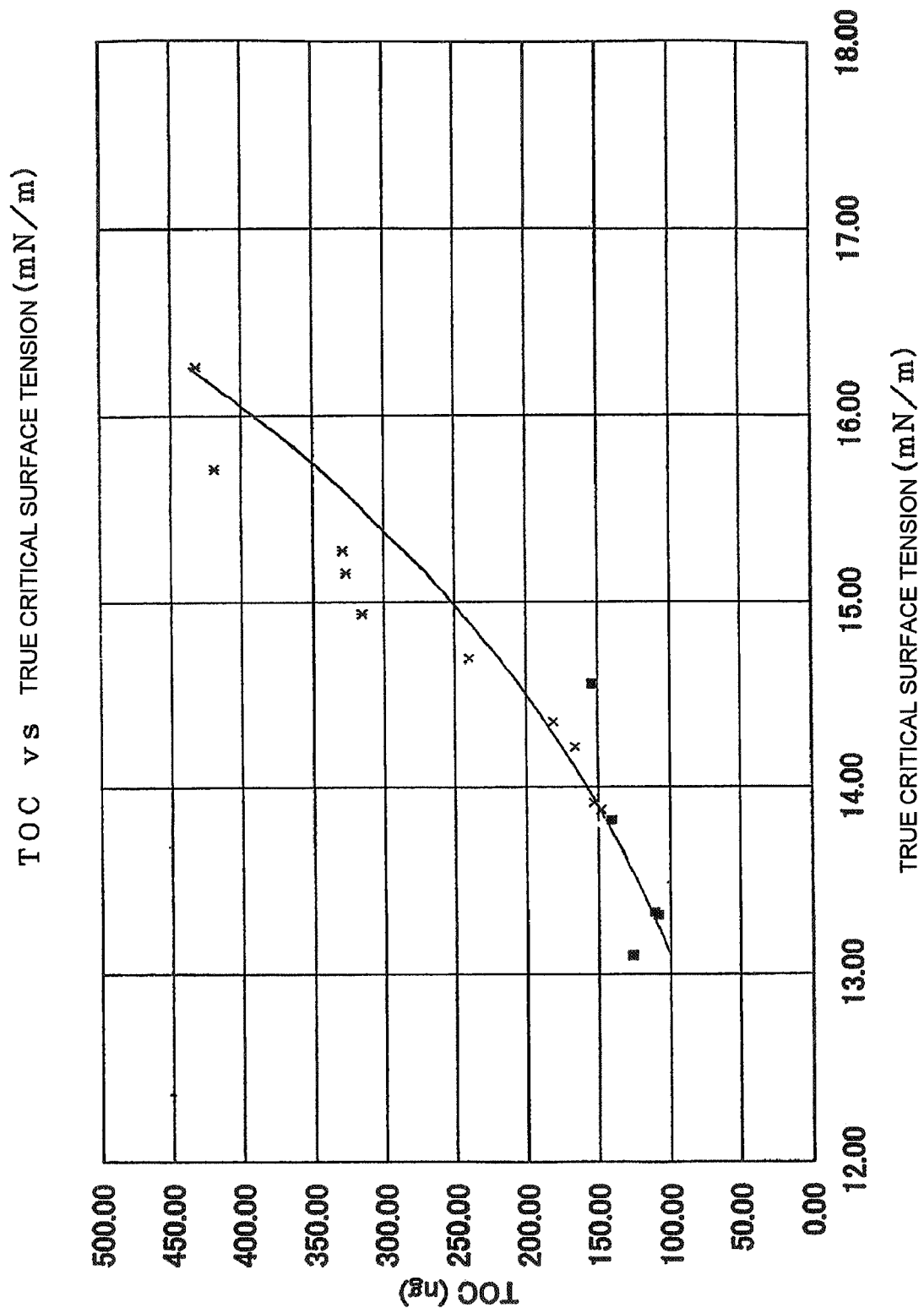
FIG. 6 is a plot diagram showing a relationship between true critical surface tensions of respective magnetic disks and durabilities of the surfaces thereof against outgas in Example 1.

Further, FIG. 6 shows a relationship between true critical surface tensions of the magnetic disks and durabilities thereof against outgas with respect to the 20 kinds of magnetic disks selected from the foregoing 53 kinds of magnetic disks.

As described above, magnetic disks have often been used in various environments. Under such circumstances, volatile organic gases such as sulfur-based organic compound, chlorine-based organic compound, dioctyl phthalate, acrylic acid, and siloxane, acid gas, and so on are emitted at a certain ratio from various organic materials such as adhesives and plastic materials that are used in a magnetic disk apparatus. Therefore, when the organic gas is adsorbed to a magnetic disk under high temperature and high humidity, interaction occurs between the organic gas and a lubricant of a lubrication layer. As a result, when a magnetic recording head in a flying operation state with a low flying height (e.g. 10 nm or less) slightly contacts the medium surface at a certain probability, the lubricant, the organic compound, and so on are transferred to adhere to a slider portion and so on of the magnetic recording head. This phenomenon is called fly stiction. It is known that occurrence of the fly stiction degrades the output properties of the magnetic recording head and causes instability of the head flying properties, thereby causing serious troubles in the magnetic disk apparatus. In order to solve this problem, it is necessary to inactivate the magnetic disk surface. As an index indicative of the degree of inactivation, the true critical surface tension of this invention is considered effective. In view of this, as shown in FIG. 6, organic contamination was forcibly adhered to the magnetic disks and the adhered organic matter was quantified, thereby deriving a relationship between the contamination adhering to the magnetic disks and the true critical surface tensions.

Specifically, the test was performed according to the following method.

20 kinds of magnetic disks were prepared and commercial silicone tape was cut into 70 mm×50 mm and loaded into HDDs along with the magnetic disks, which were then left standing for 10 hours in an environment of 60° C./RH80%. The magnetic disks after standing were taken out and the organic matter quantities (TOC) adhering to the magnetic disks were quantified by the use of a GCMS.

As shown in FIG. 6, it becomes clear that, by reducing the true critical surface tension, the organic matter quantity adhering to the magnetic disk surface also decreases. That is, this proves that the true critical surface tension is the index indicative of the degree of inactivation.

Example 2

By the use of saturated hydrocarbon that provides low surface tension, comparison was made between conventional Zisman-plot and plotting by logarithmic approximation with respect to a relationship between surface tensions of liquids and cosines of contact angles. As a sample, use was made of a magnetic disk where perfluoropolyether was applied to a thickness of 1.2 nm. Liquids that were used in contact angle measurement were as follows.

--- hexane: 20.4 mN/m, octane: 21.8 mN/m, decane: 23.9 mN/m, dodecane: 25.4 mN/m, tetradecane: 26.7 mN/m, hexadecane: 27.6 mN/m (all are saturated hydrocarbon: nonpolar)
hydrogen bonding liquid $H_2O$ (water): 72.8 mN/m
polar liquid $CH_2I_2$ (methylene iodide): 50.8 mN/m,
$C_2H_6O_2$ (ethylene glycol): 48.0 mN/m

---

Figure 7:
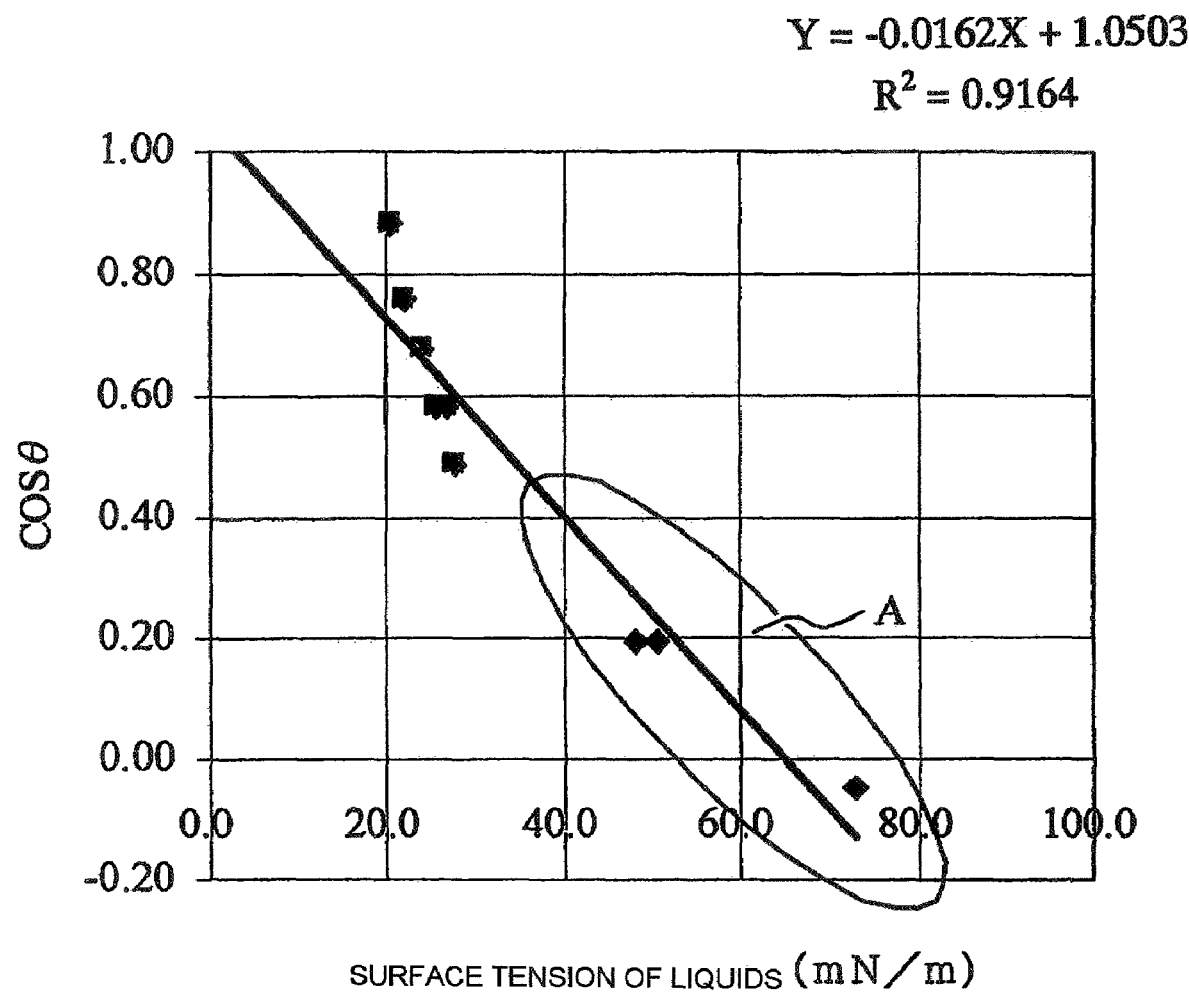
FIG. 7 is a graph where a relationship between surface tensions of liquids and cosines of contact angles is linearly approximated (Zisman-plot) in Example 2.
Figure 8:
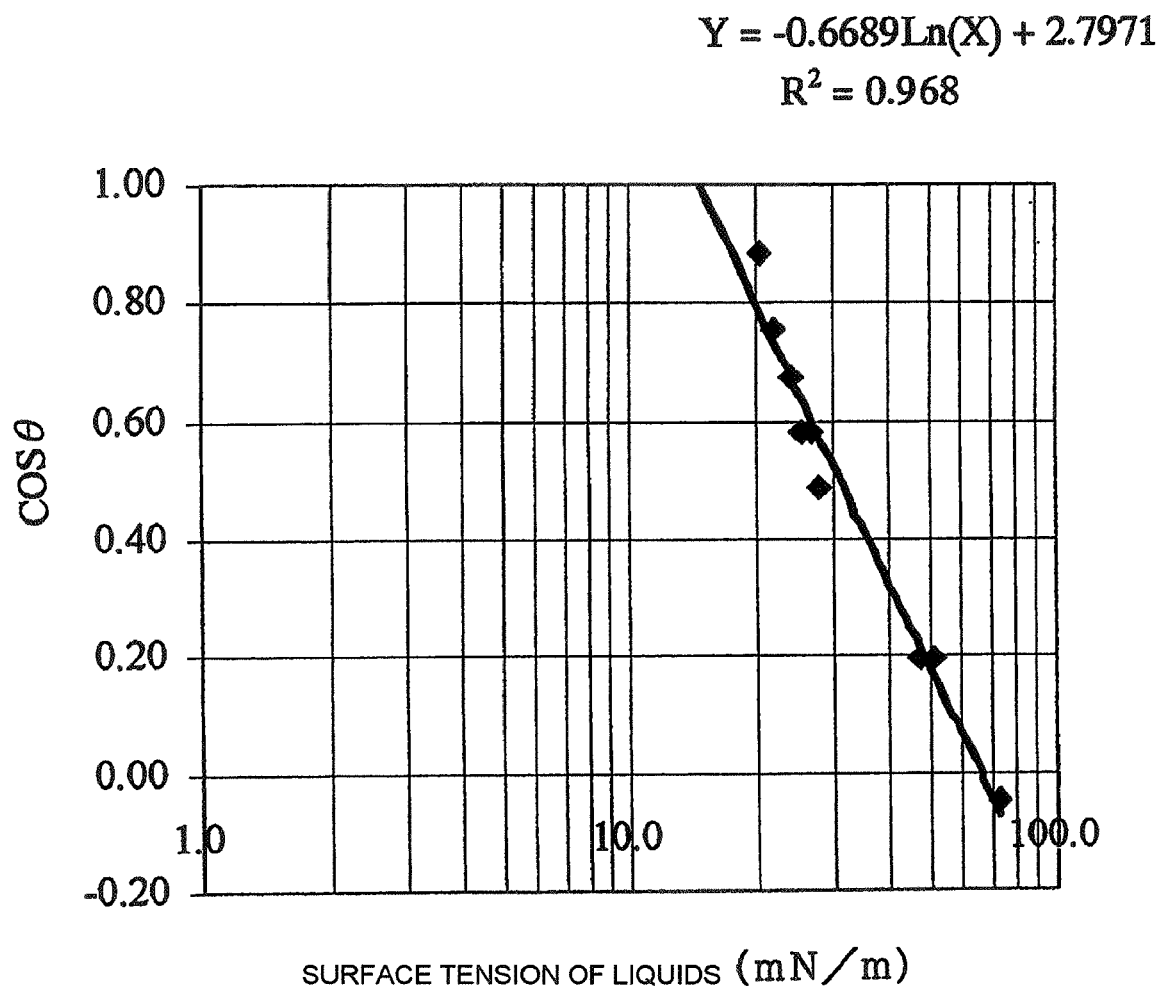
FIG. 8 is a graph where a relationship between surface tensions of liquids and cosines of contact angles is logarithmically approximated (Zisman-plot) in Example 2.

FIG. 7 shows conventional Zisman-plot while FIG. 8 shows plotting by logarithmic approximation of this invention.

The results of contact angles of the respective liquid samples are as follows.

hexane: 28.1°
octane: 40.8°
decane: 47.6°
dodecane: 54.3°
tetradecane: 54.5°
hexadecane: 61.0°
water: 92.8°
methylene iodide: 78.7°
ethylene glycol: 78.7°

As seen from FIG. 7, in conventional linear plotting (dotted line) using only saturated hydrocarbon proposed by Zisman, as described above, the problems of (1) large deviation from Zisman-plot occurs in a region (A) of high surface tension, (2) deviation occurs in a region of low surface tension when approximation is performed using all liquids (solid line), and (3) polar, nonpolar, and hydrogen bonding liquids form respective groups so that univocal expression is not possible [a saturated hydrocarbon group, a polar liquid group (surface tension is intermediate), and a hydrogen bonding liquid group are separated) are observed also in the case of the magnetic disk. This phenomenon is considered common to any solid body surfaces.

Accordingly, the critical surface tension proposed by Zisman represents a critical value with respect to saturated hydrocarbon (i.e. nonpolar) and is not effective to all energies. However, when logarithmically approximated, as shown in FIG. 8, it is possible to achieve a definition that is univocally determined, by deriving a critical value using all of polar, nonpolar, and hydrogen bonding liquids.

From the foregoing, it is proved that the true critical surface tension utilizing logarithmic approximation, which is defined by this invention, can fully solve two points of (1) a relationship between surface tensions of liquids and cos θ does not become a linear relationship particularly when the surface tensions of the liquids become large and (2) depending on the presence of a hydrogen bonding property, polarity, and nonpolarity possessed by liquids, plotted points are divided into groups and do not form one straight line, which have been the problems about the conventional critical surface tension by linear approximation proposed by Zisman.

Example 3

(1) Manufacture of Magnetic Disk

A magnetic disk having a layer structure shown in FIG. 3 was manufactured in the following manner.

Aluminosilicate glass was formed into a disk shape to obtain a glass disk. By applying grinding, precision polishing, end-face polishing, precision cleaning, and chemical strengthening to the obtained glass disk, a flat, smooth, and high-rigidity glass substrate for a magnetic disk was obtained. This glass substrate was a 2.5-inch magnetic disk substrate having a diameter of 65 mm, an inner diameter of 20 mm, and a disk thickness of 0.635 mm. Here, when the surface roughness of the obtained glass substrate was observed by the use of an AFM (Atomic Force Microscope), it was confirmed to be a smooth surface having Rmax of 3.96 nm and Ra of 0.36 nm.

Then, by the use of a static opposed type film-forming apparatus, a seed layer 2a, an underlayer 2b, and a magnetic layer 3 were formed on the glass substrate 1 in this order by DC magnetron sputtering. Specifically, first, using an AlRu (Al: 50 atm %, Ru: 50 atm %) alloy as a sputtering target, the seed layer 2a made of the AlRu alloy and having a thickness of 30 nm was formed on the glass substrate 1 by sputtering. Then, using a CrMo (Cr: 80 atm %, Mo: 20 atm %) alloy as a sputtering target, the underlayer 2b made of the CrMo alloy and having a thickness of 20 nm was formed on the seed layer 2a by sputtering. Then, using a CoCrPtB (Cr: 20 atm %, Pt: 12 atm %, B: 5 atm %, the remainder: Co) alloy as a sputtering target, the magnetic layer 3 made of the CoCrPtB alloy and having a thickness of 15 nm was formed on the underlayer 2b by sputtering.

Then, on the disk having been formed with the magnetic layer 3, a carbon-based protection layer 4 made of carbon, hydrogen, and nitrogen was formed by the use of plasma CVD (P-CVD). Specifically, using a mixed gas in the form of a mixture of acetylene and nitrogen in the ratio of 97%:3% as a reactive gas, deposition was carried out so that the carbon-based protection layer by CVD having a thickness of 4.5 nm was formed on the magnetic layer 3. The deposition rate upon forming the carbon-based protection layer was 1 nm/s. Upon forming the protection layer, high frequency power (frequency 27 MHz) was applied to electrodes to produce plasma. Further, a bias of −300W was applied. As the thickness of the protection layer 4, the actual thickness was measured through cross-section observation by a transmission electron microscope (TEM).

In this event, P-CVD deposition may be carried out as IBD (Ion Beam Deposition) by applying a voltage to plasma, or the like.

After the formation of the carbon-based protection layer 4 in this manner, immersion cleaning was performed in pure water at 70° C. for 400 seconds, then cleaning was further performed for 400 seconds by the use of isopropyl alcohol (IPA), and then drying was performed as finish drying by the use of IPA vapor.

Next, by the use of a dipping method, a lubrication layer 5 made of a PFPE (perfluoropolyether) compound was formed on the carbon-based protection layer 4 after the pure water and IPA cleaning. Specifically, using trade name "Fomblin Z-Tetraol" manufactured by Solvay Solexis, Inc. as a material, molecular weight fractionation was performed by the use of a supercritical fluid extraction method to make an adjustment so that the weight average molecular weight (Mw) became 7400. In this event, the surface tension was 17 mN/m. The surface tension was measured by a ring method. After applying a lubricant, burning was carried out at 110° C. for 60 minutes. The thickness of the lubrication layer 5 after the burning was 1.2 nm.

In this manner, the magnetic disk 10 was manufactured.

When the surface roughness of the obtained magnetic disk 10 was observed by the use of the AFM, it was confirmed to be a smooth surface having Rmax of 4.21 nm and Ra of 0.41 nm. Further, the glide height was measured to be 4.5 nm. In order to stably achieve a flying height of the magnetic head being 10 nm or less, the glide height of the magnetic disk is preferably set to 5 nm or less.

(2) Performance Evaluation of Magnetic Disk

With respect to the magnetic disk obtained in the foregoing (1), various performances were evaluated and analyzed in the following manner.

(a) Measurement of Surface Tension

As liquids that were used, selection was made of the following five kinds whose surface tensions were known.

hydrogen bonding liquid water: 72.8 mN/m
polar liquid $CH_2I_2$: 50.8 mN/m, $C_2H_6O_2$: 48.0 mN/m
nonpolar liquid $C_{14}H_{30}$: 26.7 mN/m, hexane: 20.4 mN/m Note that hydrogen bonding, polar, and nonpolar liquids may be other than the foregoing.

1 μL of the foregoing liquid was dropped onto the surface of the obtained magnetic disk 10 and a contact angle was measured after 10 seconds from dropping. The liquid amount was set to 1 μL because each liquid exhibited a substantially constant contact angle at 1 μL or more regardless of the sample. Duplicate measurement was carried out twice per liquid and the mean value thereof was derived as a contact angle. For the contact angle measurement, use was made of a contact angle measuring system "VCA Video Contact Angle System" of Analytical Technology Incorporated. After the measurement, cosines (cos θ) of the obtained contact angles were derived and plotted against values of the surface tensions of the respective liquids.

The results of contact angles of the respective liquid samples are as follows.

water: 92.7°
methylene iodide: 72.5°
ethylene glycol: 74.9°
tetradecane: 61.9°
hexane: 35°

Figure 9:
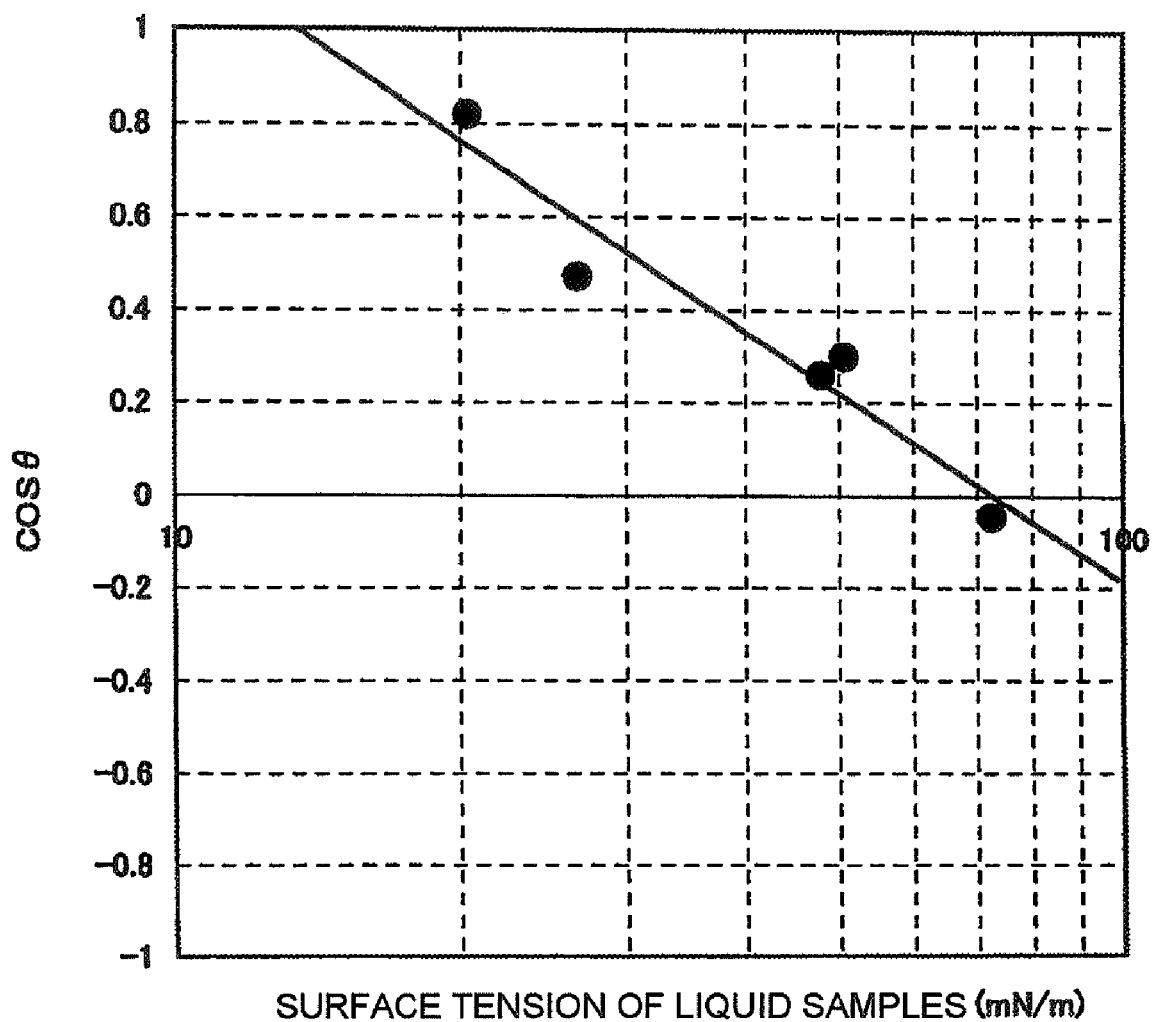
FIG. 9 is a graph where a relationship between surface tensions of liquids and cosines of contact angles is logarithmically approximated (Zisman-plot) in Example 3.

As shown in FIG. 9, a logarithmic expression given as Y=a×ln (X)+b was used as an approximate expression with respect to the respective plots and coefficients a and b were determined by the use of the method of least squares where the sum of squares of errors becomes minimum, thereby approximating the plots. Then, the logarithmically approximated curve was extrapolated to derive a value of surface tension at a point extrapolated to a point where the cosine (cos θ) becomes 1 (i.e. a point that is completely wet) and this value was given as a surface tension of the magnetic disk surface. The surface tension of the magnetic disk exhibited 13.43 mN/m.

(b) TOP Test

A fly stiction test was performed in the following manner.

The magnetic disk obtained in the foregoing (1) and a magnetic recording head having a flying height of 10 nm were installed in a magnetic disk apparatus. The magnetic head was mounted with a PZT sensor in advance so that the PZT sensor was able to receive a vibration signal upon occurrence of contact between the head and the magnetic disk. Thereafter, the apparatus was put in a pressure reducing chamber where the pressure was gradually reduced from the atmospheric pressure so that the magnetic head was brought into contact with the magnetic disk and then adsorbed thereto. When the magnetic head is brought into contact with and adsorbed to the magnetic disk, the PZT sensor reacts thereto and produces a signal. The pressure on this occasion is called a TDP (Touch Down Pressure). Thereafter, the pressure was gradually returned and the pressure upon separation of the adsorbed magnetic head was recorded. The pressure on this occasion is called a TOP (Take Off Pressure). TDP is generally related to the glide height of a magnetic disk and TDP of this magnetic disk was 0.0425 MPa. As an index of fly stiction, TOP is used. That is, the fly stiction property is more excellent when the pressure at which the adsorbed head separates is lower. This means that even once adsorbed, the head immediately separates from the magnetic disk. TOP of this magnetic disk exhibited 0.061 MPa. In general, it is said that the atmospheric pressure in an airplane is about 0.071 MPa at minimum and, therefore, a magnetic disk is required to have a TOP of 0.071 MPa or less. This magnetic disk has a TOP of 0.061 MPa, which is sufficiently low, and thus it is clear that this magnetic disk is excellent in fly stiction property.

(c) LUL Durability Test

An LUL durability test was performed using a 2.5-inch HDD that rotates at 5400 rpm and a magnetic head having a flying height of 10 nm. An NPAB (negative pressure type) slider was used as a slider of the magnetic head and a GMR element was used as a reproduction element. The magnetic disk 10 was mounted in this HDD and the LUL operation was continuously carried out by the magnetic head. By measuring the number of LUL times the HDD endured without failure, the LUL durability was evaluated. The results of the LUL durability test exhibited durability of 1,200,000 times.

Example 4

In the manufacture of a magnetic disk of Example 1, when a lubrication layer 5 was formed, use was made of trade name "Fomblin Z-Tetraol" manufactured by Solvay Solexis, Inc. and trade name "Fomblin Z-DOL" manufactured by Solvay Solexis, Inc. as materials and both were subjected to molecular weight fractionation by the use of a supercritical fluid extraction method and then were mixed together in the ratio of 1:1. In this event, Mw thereof were adjusted to 5800 and 3000, respectively. The surface tension was 19.4 mN/m. The thickness of the lubrication layer was adjusted to 1.2 nm like in Example 1.

The formation of the lubrication layer 5 was the same as that in Example 1 except the material. Except these points, the magnetic disk 10 was manufactured by the same method as in Example 1.

With respect to this magnetic disk 10, performance evaluation was carried out like in Example 1. The results are shown in Table 1.

Examples 5 to 8, Comparative Examples 1 to 3

In the manufacture of a magnetic disk 10 of Example 1, a lubrication layer 5 was formed by the use of a lubricant of a kind and weight average molecular weight shown in Table 1 and, depending on the case, a surface treatment by hydrofluoroether was carried out. Except these, the magnetic disk 10 was manufactured like in Example 1.

With respect to the obtained magnetic disk 10, performance evaluation was carried out like in Example 1. The results are shown in Table 1.

(Surface Treatment by Hydrofluoroether)

The surface treatment by hydrofluoroether (HFE) was performed by the use of a liquid composition composed of a hydrofluoroether compound having a $C_4F_9$—O—$CH_3$ structure. The molecular weight of this hydrofluoroether is 250. Further, the surface tension is 13.6 mN/m. By depositing this hydrofluoroether composition on the surface of the lubrication layer 5 by the use of a vapor deposition method (treatment time 60 seconds), hydrofluoroether was brought into contact with the magnetic disk surface.

TABLE 1

| | Kind of Lubricant [Weight Average Molecular Weight] | Surface Tension of Lubricant (mN/m) | Presence of Hydrofluoroether Treatment | Surface Tension of Magnetic Disk (mN/m) | TOP (MPa) | Number of Load/ Unload (LUL) Durable Times |
|---|---|---|---|---|---|---|
| Example 3 | A [7400] | 17.0 | No | 13.43 | 0.061 | 1,200,000 Times |
| Example 4 | A [5800] B [3000] | 19.4 | No | 15.86 | 0.066 | 1,00,000 Times |
| Comparative Example 1 | B [3300] | 20.4 | No | 17.12 | 0.072 | 100,000 Times |
| Example 5 | A [3000] | 21.2 | Yes | 16.82 | 0.070 | 800,000 Times |
| Example 6 | A [4000] | 20.4 | Yes | 16.53 | 0.066 | 800,000 Times |
| Example 7 | A [5000] | 19.7 | Yes | 15.54 | 0.064 | 970,000 Times |
| Comparative Example 2 | A [3000] | 21.2 | No | 18.12 | 0.076 | 200,000 Times |
| Comparative Example 3 | A [4000] | 20.4 | No | 17.08 | 0.072 | 400,000 Times |
| Example 8 | A [5000] | 19.7 | No | 16.12 | 0.065 | 800,000 Times |

[note]
(1) Protection layers (carbon-based protection layers) were all formed through deposition by the use of a plasma CVD method.
(2) A lubricant A is a lubricant obtained by using "Fomblin Z-Tetraol" manufactured by Solvay Solexis, Inc. as a material and refining it by the use of a supercritical fluid extraction method to make an adjustment to a predetermined molecular weight distribution.

A perfluoropolyether compound contained in the lubricant A as a main component has a structure expressed by:

General Formula (I)

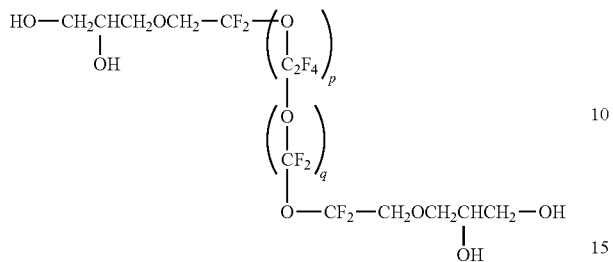

(in the formula, p and q represent integers equal to 1 or more, respectively).

(3) A lubricant B is a lubricant obtained by using "Fomblin Z-DOL" manufactured by Solvay Solexis, Inc. as a material and refining it by the use of a supercritical fluid extraction method to make an adjustment to a predetermined molecular weight distribution. Note that a lubricant B in Comparative Example 1 is an unrefined product of the foregoing "Fomblin Z-DOL".

A perfluoropolyether compound contained in the lubricant B as a main component has a structure expressed by:

General Formula (II)

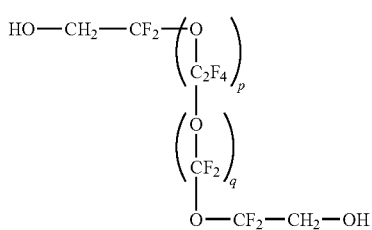

(in the formula, p and q represent integers equal to 1 or more, respectively).

According to the solid body surface evaluation method of this invention, by evaluating surface tension of the surface of a solid body by the use of hydrogen bonding, polar, and nonpolar liquids, it becomes possible to univocally define the surface tension of the solid body surface so that the true surface tension of the solid body surface can be provided.

Further, according to the magnetic disk of this invention, by reducing surface energy of the magnetic disk, the fly stiction can be sufficiently prevented in a flying height of a magnetic recording head being 10 nm or less.

Although this invention has been described above in detail with reference to the examples, it is needless to say that various changes can be made by a person skilled in the art without departing from the scope of claims.

What is claimed is:

1. A magnetic disk having at least a magnetic layer, a protection layer, and a lubrication layer formed on a substrate in this order, wherein:

when selection is made of at least three liquid samples including a liquid sample containing a nonpolar substance, a liquid sample containing a polar substance, and a liquid sample containing a hydrogen bonding substance, and having mutually different surface tensions, contact angles between the respective liquid samples and a surface of the magnetic disk are measured to thereby derive a correlation between cosines (Y) of the contact angles and surface tensions (X) of the liquid samples as a natural logarithmic function by a method of least squares, and a value of X that is calculated by substituting 1 for Y in said correlation is given as a true critical surface tension of said magnetic disk, the true critical surface tension is greater than 0 and no greater than 17 mN/m (milli Newton/meter), wherein the protection layer contains carbon, hydrogen and nitrogen, a content of the hydrogen is set to 3 atm % or more and less than 20 atm % relative to a total of the protection layer, a content of the nitrogen relative to the carbon is 4 to 12 atm %, the lubrication layer contains only a perfluoropolyether compound having weight average molecular weight of 5000 or more, and a hydrofluoroether film is formed on a surface of the lubrication layer.

2. A magnetic disk according to claim 1, wherein:
a surface tension of a lubricant forming the lubrication layer is 20 mN/m or less.

3. A magnetic disk according to claim 1 or 2, wherein:
the lubrication layer contains a perfluoropolyether compound having hydroxyl groups as terminal functional groups.

4. A magnetic disk according to claim 1 or 2, wherein: the magnetic disk is for installation in a hard disk drive of a load/unload system.

5. A magnetic disk according to claim 1 or 2, wherein: the lubrication layer has a thickness within a range of 0.5 to 1.5 nm.

* * * * *